US011304703B2

(12) United States Patent
Pilletere et al.

(10) Patent No.: US 11,304,703 B2
(45) Date of Patent: Apr. 19, 2022

(54) LIGATION CLIP REMOVAL DEVICE (71) Applicant: Covidien LP, Mansfield, MA (US)

(72) Inventors: Roy J. Pilletere, North Haven, CT (US); Eric Brown, Haddam, CT (US); Gregory R. Morck, Middletown, CT (US); Saumya Banerjee, Hamden, CT (US); Justin Thomas, New Haven, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 234 days.

(21) Appl. No.: 16/364,648

(22) Filed: Mar. 26, 2019

(65) Prior Publication Data

US 2019/0357913 A1    Nov. 28, 2019

Related U.S. Application Data (60) Provisional application No. 62/676,293, filed on May 25, 2018.

(51) Int. Cl.
*A61B 17/128* (2006.01)
*A61B 17/29* (2006.01)

(52) U.S. Cl.
CPC .......... *A61B 17/1285* (2013.01); *A61B 17/29* (2013.01); *A61B 2017/2933* (2013.01); *A61B 2017/2947* (2013.01)

(58) Field of Classification Search
CPC ... A61B 17/128; A61B 17/1285; A61B 17/29; A61B 17/28; A61B 17/2812;

(Continued)

(56) References Cited

U.S. PATENT DOCUMENTS 3,439,523 A    4/1969 Wood
3,713,533 A    1/1973 Reimels
(Continued)

FOREIGN PATENT DOCUMENTS

BE    654195 A    2/1965
CN    204839635 U    12/2015
CN    106264647 A    1/2017
(Continued)

OTHER PUBLICATIONS

U.S. Appl. No. 62/655,854, filed Apr. 11, 2018, inventor Justin Thomas.

(Continued)

*Primary Examiner* — Wade Miles
*Assistant Examiner* — Mikail A Mannan (57) ABSTRACT

A ligation clip removal device includes an elongate body, a tool assembly, and a drive member. The tool assembly is supported on a distal portion of the elongate body and includes a first jaw and a second jaw pivotably supported in relation to the first jaw between an open position and a clamped position. Each of the first and second jaws includes a clip engagement surface that defines a recess having a longitudinal portion and a first transverse portion that intersects the longitudinal portion. The longitudinal portions of the recesses are configured to receive a leg of a ligation clip and the first transverse portion of the recess is configured to receive a portion of a boss of the ligation clip. The drive member is engaged with and movable in relation to the tool assembly to move the first and second jaws between the open and clamped positions.

10 Claims, 5 Drawing Sheets

(58) Field of Classification Search
CPC .............. A61B 17/2816; A61B 17/282; A61B 2017/0488; A61B 2017/2933; A61B 2017/2947; A61B 2017/2808
See application file for complete search history.

(56) References Cited

U.S. PATENT DOCUMENTS

| | | |
|---|---|---|
| 4,076,120 A | 2/1978 | Carroll et al. |
| 4,146,130 A | 3/1979 | Samuels et al. |
| 4,187,712 A | 2/1980 | Samuels et al. |
| 4,212,303 A | 7/1980 | Nolan |
| 4,212,390 A | 7/1980 | Raczkowski et al. |
| 4,294,355 A | 10/1981 | Jewusiak et al. |
| 4,344,531 A | 8/1982 | Giersch |
| 4,346,869 A | 8/1982 | MacNeill |
| 4,361,229 A | 11/1982 | Mericle |
| 4,390,019 A | 6/1983 | LeVeen et al. |
| 4,412,617 A | 11/1983 | Cerwin |
| 4,418,694 A | 12/1983 | Beroff et al. |
| 4,449,531 A | 5/1984 | Cerwin et al. |
| 4,485,953 A | 12/1984 | Rothfuss |
| 4,487,205 A | 12/1984 | Di Giovanni et al. |
| 4,550,729 A | 11/1985 | Cerwin et al. |
| 4,696,396 A | 9/1987 | Samuels |
| 4,726,372 A | 2/1988 | Perlin |
| 4,834,096 A | 5/1989 | Oh et al. |
| 4,936,447 A | 6/1990 | Peiffer |
| 4,942,886 A | 7/1990 | Timmons |
| 4,961,499 A | 10/1990 | Kulp |
| 4,971,198 A | 11/1990 | Mericle |
| 4,972,949 A | 11/1990 | Peiffer |
| 5,046,611 A | 9/1991 | Oh |
| 5,046,624 A | 9/1991 | Murphy et al. |
| 5,050,272 A | 9/1991 | Robinson et al. |
| 5,062,846 A | 11/1991 | Oh et al. |
| 5,100,416 A | 3/1992 | Oh et al. |
| 5,201,416 A | 4/1993 | Taylor |
| 5,279,416 A | 1/1994 | Malec et al. |
| 5,423,831 A | 6/1995 | Nates |
| 5,564,262 A | 10/1996 | Bevis et al. |
| 5,634,930 A | 6/1997 | Thornton et al. |
| 5,676,676 A | 10/1997 | Porter |
| 5,697,942 A | 12/1997 | Palti |
| 5,713,912 A | 2/1998 | Porter |
| 5,846,255 A | 12/1998 | Casey |
| 5,908,430 A | 6/1999 | Appleby |
| 5,921,991 A | 7/1999 | Whitehead et al. |
| 6,044,971 A | 4/2000 | Esposito et al. |
| 6,158,583 A | 12/2000 | Forster |
| 6,217,590 B1 | 4/2001 | Levinson |
| 6,228,097 B1 | 5/2001 | Levinson et al. |
| 6,273,253 B1 | 8/2001 | Forster et al. |
| 6,306,150 B1 | 10/2001 | Levinson |
| 6,349,727 B1 | 2/2002 | Stewart, Jr. |
| 6,391,035 B1 | 5/2002 | Appleby et al. |
| 6,419,682 B1 | 7/2002 | Appleby et al. |
| 6,421,920 B1 | 7/2002 | Jensen |
| 6,439,727 B1 | 8/2002 | Koide |
| 6,460,700 B2 | 10/2002 | Weisshaupt |
| 6,460,749 B1 | 10/2002 | Levinson et al. |
| 6,780,195 B2 | 8/2004 | Porat |
| 6,824,547 B2 | 11/2004 | Wilson, Jr. et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,052,504 B2 | 5/2006 | Hughett |
| 7,131,977 B2 | 11/2006 | Fowler |
| 7,144,402 B2 | 12/2006 | Kuester, III |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,452,368 B2 | 11/2008 | Liberatore et al. |
| 7,585,304 B2 | 9/2009 | Hughett |
| 7,628,272 B2 | 12/2009 | Wiedenbein |
| 7,857,129 B2 | 12/2010 | Iaconi-Forrer et al. |
| 8,042,687 B2 | 10/2011 | Cannady |
| 8,312,992 B2 | 11/2012 | Disch |
| 8,403,138 B2 | 3/2013 | Weisshaupt et al. |
| 8,425,515 B2 | 4/2013 | Gamache et al. |
| 8,627,955 B2 | 1/2014 | Weisshaupt et al. |
| 8,839,954 B2 | 9/2014 | Disch |
| 8,888,398 B2 | 11/2014 | Werth |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,517,178 B2 | 12/2016 | Chancibot |
| D808,522 S | 1/2018 | Cannady et al. |
| 9,855,053 B2 | 1/2018 | Bagaoisan et al. |
| 10,130,373 B2 | 11/2018 | Castro et al. |
| 10,136,898 B2 | 11/2018 | Schmidt et al. |
| 10,905,451 B2 * | 2/2021 | Kappel ............... A61B 18/1445 |
| 10,925,615 B2 * | 2/2021 | Deville ................ A61B 17/122 |
| 2002/0046961 A1 | 4/2002 | Levinson et al. |
| 2002/0177863 A1 | 11/2002 | Mandel et al. |
| 2004/0172057 A1 * | 9/2004 | Guillebon ............... A61B 17/29 |
| | | 606/207 |
| 2004/0199178 A1 | 10/2004 | Small |
| 2005/0165423 A1 | 7/2005 | Gallagher et al. |
| 2005/0165424 A1 | 7/2005 | Gallagher et al. |
| 2006/0089659 A1 | 4/2006 | Small |
| 2006/0124485 A1 | 6/2006 | Kennedy |
| 2006/0217749 A1 | 9/2006 | Wilson et al. |
| 2007/0083218 A1 | 4/2007 | Morris |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2008/0015566 A1 * | 1/2008 | Livneh ................. A61B 17/295 |
| | | 606/37 |
| 2009/0088783 A1 | 4/2009 | Kennedy et al. |
| 2009/0171380 A1 | 7/2009 | Whiting |
| 2011/0184459 A1 * | 7/2011 | Malkowski ........ A61B 17/2909 |
| | | 606/206 |
| 2011/0224700 A1 | 9/2011 | Schmidt et al. |
| 2011/0295291 A1 | 12/2011 | Trivisani |
| 2012/0080336 A1 * | 4/2012 | Shelton, IV ......... A61B 17/064 |
| | | 206/339 |
| 2012/0083803 A1 | 4/2012 | Patel et al. |
| 2012/0226291 A1 | 9/2012 | Malizia et al. |
| 2013/0245651 A1 | 9/2013 | Schmidt et al. |
| 2013/0253540 A1 | 9/2013 | Castro et al. |
| 2013/0261642 A1 | 10/2013 | Willett et al. |
| 2014/0054192 A1 | 2/2014 | Chancibot |
| 2014/0243862 A1 | 8/2014 | Bagaoisan et al. |
| 2014/0276970 A1 | 9/2014 | Messerly et al. |
| 2016/0015253 A1 | 1/2016 | Roop et al. |
| 2016/0151073 A1 | 6/2016 | Castro et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0196637 A1 * | 7/2017 | Shelton, IV ..... A61B 17/07207 |
| 2017/0209151 A1 | 7/2017 | Brown |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0116674 A1 | 5/2018 | Baril |
| 2018/0168659 A1 | 6/2018 | Bagaoisan et al. |
| 2018/0185029 A1 | 7/2018 | Lebens, III |
| 2018/0228492 A1 | 8/2018 | Aranyi et al. |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |
| 2019/0133590 A1 | 5/2019 | Richard |

(56) References Cited

U.S. PATENT DOCUMENTS

2019/0159782 A1    5/2019  Kamaraj et al.
2021/0052334 A1*  2/2021  Johnson ................. A61B 34/37

FOREIGN PATENT DOCUMENTS

| DE | 10116168 A1 | 11/2001 |
|----|-------------|---------|
| GB | 2353710 A | 3/2001 |
| WO | 2017059587 A1 | 4/2017 |

OTHER PUBLICATIONS

U.S. Appl. No. 62/655,882, filed Apr. 11, 2018, inventor Justin Thomas.
U.S. Appl. No. 62/661,842, filed Apr. 24, 2018, inventor Justin Thomas.
U.S. Appl. No. 62/717,958, filed Aug. 13, 2018, inventor Justin Thomas.
U.S. Appl. No. 62/721,178, filed Aug. 22, 2018, inventor Justin Thomas.
U.S. Appl. No. 16/158,368, filed Oct. 12, 2018, inventor Roy Pilletere.
Chinese International PCT Application No. PCT/CN2018/078294 filed Mar. 7, 2018, Covidien LP.
U.S. Appl. No. 13/972,582, filed Aug. 21, 2013, inventor Manoj Patel.
European Search Report dated Aug. 26, 2019, issued in EP Appln. No. 19176599.
European Office Action dated Apr. 22, 2021, issued in corresponding EP Appln. No. 19 176 599, 6 pages.
European Office Action dated Nov. 25, 2021, issued in corresponding EP Appln. No. 19176599, 8 pages.

* cited by examiner

LIGATION CLIP REMOVAL DEVICE

CROSS-REFERENCE TO RELATED APPLICATION

This application claims the benefit of and priority to U.S. Provisional Patent Application No. 62/676,293 filed May 25, 2018, the entire disclosure of which is incorporated by reference herein.

BACKGROUND

1. Technical Description

The present disclosure is directed to a ligation clip removal device, and more particularly, to ligation clip removal devices that include jaws that are configured to compress a latched ligation clip to unlatch the ligation clip.

2. Background of Related Art

Certain ligation clips are designed to be removable from a body vessel after a surgical procedure has been completed. Typically, with polymeric ligation clips that have a curved body, in order to remove the clip from the body tissue, the ligation clip is clamped between two jaws to deform and straighten the ligation clip. When the ligation clip is straightened, a latch on jaws of the ligation clip releases to allow the ligation clip to open.

Current ligation clip removal devices do not securely support the ligation clip to be opened within or between jaws of the removal device. As such, when a force is applied to the ligation clip by the jaws of the removal device, the ligation clip has a tendency to twist and lose perpendicularity with the jaws of the removal device. When this occurs, a body of the ligation clip may not be straightened and, thus, the latch on the ligation clip may not open. This problem may make it more difficult and time consuming to remove the ligation clip from the body vessel.

A continuing need exists in the art for a ligation clip removal device that is configured to support a ligation clip in a stable manner on the device to quickly and easily remove the ligation clip from a body vessel.

SUMMARY

One aspect of the present disclosure is directed to a ligation clip removal device including an elongate body, a tool assembly, and a drive member. The elongate body has a proximal portion and a distal portion. The tool assembly is supported on the distal portion of the elongate body and includes a first jaw, and a second jaw pivotably supported in relation to the first jaw between an open position and a clamped position. Each of the first and second jaws includes a clip engagement surface. The clip engagement surface of at least one of the first or second jaws defines a recess having a longitudinal portion and a first transverse portion that intersects the longitudinal portion. The longitudinal portion of the recess is configured to receive a leg of a ligation clip and the first transverse portion of the recess is configured to receive a portion of a boss of the ligation clip. The drive member is engaged with and movable in relation to the tool assembly to move the first and second jaws between the open and clamped positions.

In embodiments, the distal portion of the elongate body includes a clevis and each of the first and second jaws is pivotably supported on the clevis.

In some embodiments, each of the first and second jaws defines a cam slot and the drive member includes a cam member that is positioned within the cam slots of the first and second jaws such that movement of the drive member in relation to the tool assembly moves the first and second jaws between the open and clamped positions.

In certain embodiments, the elongate body defines a longitudinal bore and the drive member is movable within the longitudinal bore.

In embodiments, each of the first and second jaws defines the recess.

In some embodiments, the recess includes a second transverse portion that is spaced from the first transverse portion and intersects the longitudinal portion.

In certain embodiments, the first transverse portion of the recess is perpendicular to the longitudinal portion of the recess.

Another aspect of the present disclosure is directed to a tool assembly including a first jaw and a second jaw pivotably supported in relation to the first jaw between an open position and a clamped position. Each of the first and second jaws includes a clip engagement surface. The clip engagement surface of at least one of the first or second jaws defines a recess having a longitudinal portion and a first transverse portion that intersects the longitudinal portion. The longitudinal portion of the recess is positioned and configured to receive a leg of a ligation clip and the first transverse portion of the recess is positioned and configured to receive a portion of a boss of the ligation clip.

Another aspect of the present disclosure is directed to a method for removing a ligation clip from body tissue including positioning a tool assembly having first and second jaws in an open position about a ligation clip that is in a latched state; moving the first and second jaws of the tool assembly from the open position towards an intermediate position to position the ligation clip within a recess defined in at least one jaw of the first or second jaws of the tool assembly to secure the ligation clip between the first and second jaws; and moving the first and second jaws of the tool assembly from the intermediate position to a clamped position to move the ligation clip from the latched state to an unlatched state.

In embodiments, moving the first jaw of the tool assembly in relation to the second jaw of the tool assembly from the open position to the intermediate position to position the ligation clip within the recess in the at least one of the first or second jaws includes positioning the ligation clip within the recess in each of the first and second jaws.

In some embodiments, moving the first and second jaws of the tool assembly from the intermediate position to the clamped position to move the ligation clip from the latched state to the unlatched state includes deforming a body of the ligation clip from a curved configuration to a straightened configuration to release a latch of the ligation clip.

BRIEF DESCRIPTION OF THE DRAWINGS

Various embodiments of the presently disclosed ligation clip removal device are described herein below with reference to the drawings, wherein.

DETAILED DESCRIPTION OF EMBODIMENTS

The presently disclosed ligation clip removal device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 1:
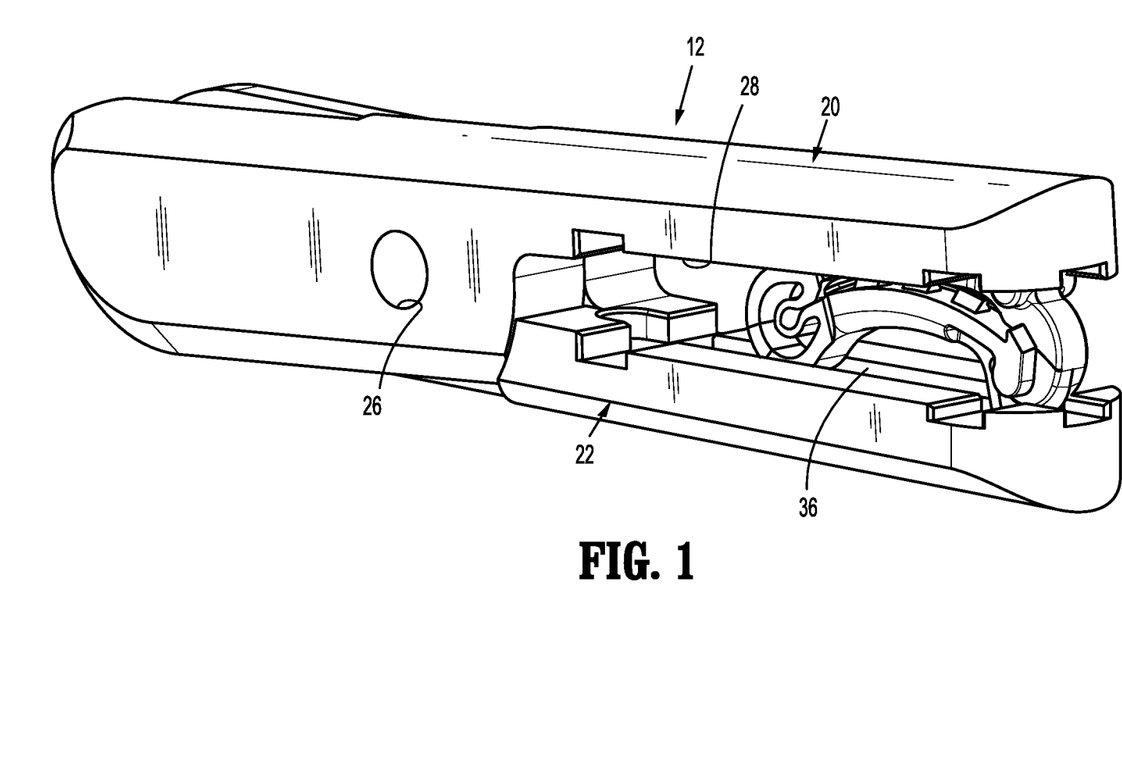
FIG. 1 is a side perspective view of an exemplary embodiment of a tool assembly of the presently disclosed ligation clip removal device with a ligation clip positioned between jaws of the tool assembly in a latched state, and the jaws in an intermediate position.
Figure 2:
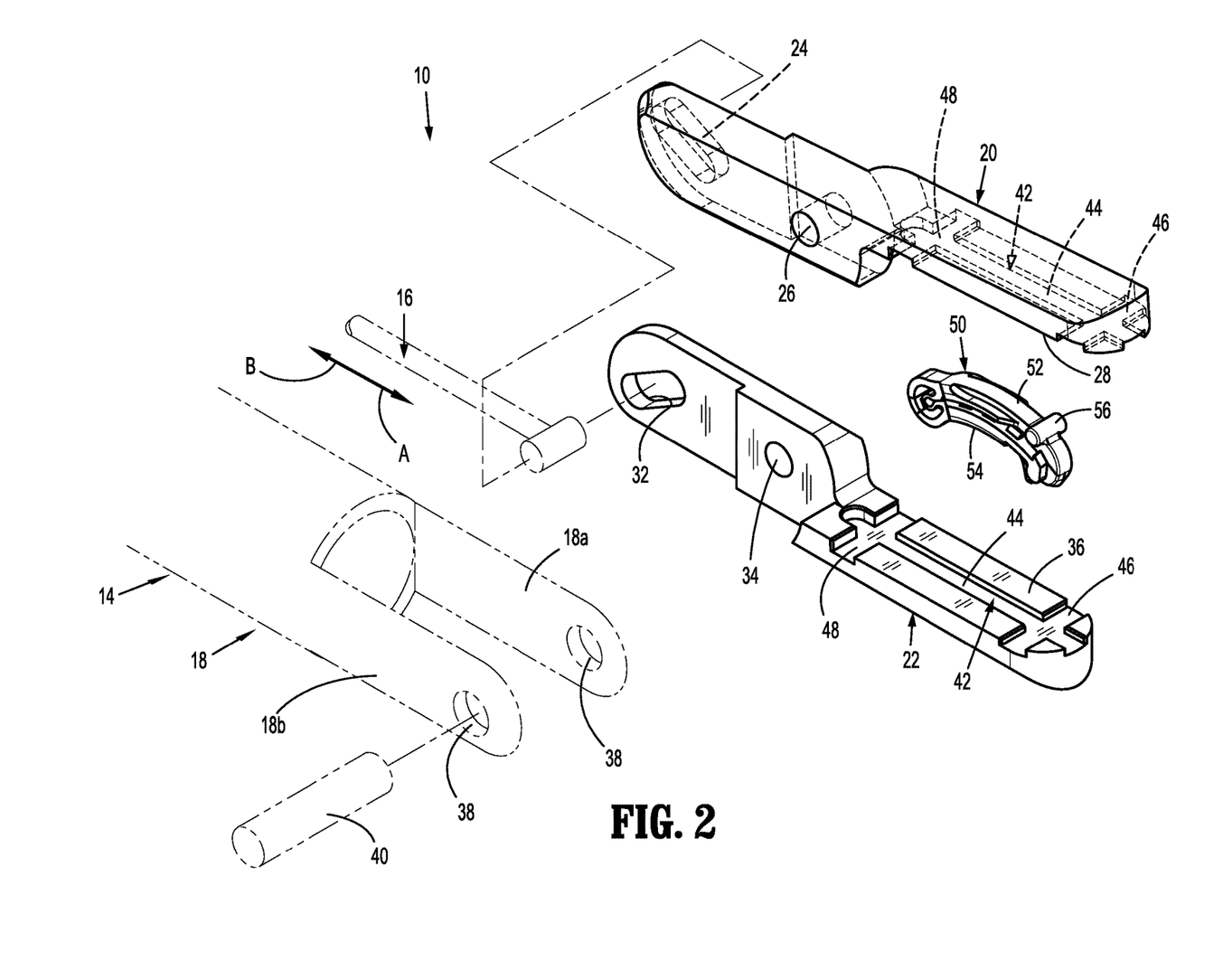
FIG. 2 is a side perspective, exploded view of a distal portion of the presently disclosed ligation clip removal device including the tool assembly shown in FIG. 1, an elongate body shown in phantom, and the ligation clip in the latched state.

Referring to FIGS. 1 and 2, the presently disclosed ligation clip removal device is shown generally as removal device 10 and includes a tool assembly 12 and an elongate body 14 (FIG. 2). Although not shown, a proximal portion of the elongate body 14 can be coupled to a handle assembly that is adapted to actuate a drive member 16 that extends through the elongate body 14 as described in further detail below. Alternately, the proximal portion of the elongate body 14 can be adapted to be coupled to a robotic system for robotically operating the presently disclosed ligation clip removal device 10.

Figure 7:
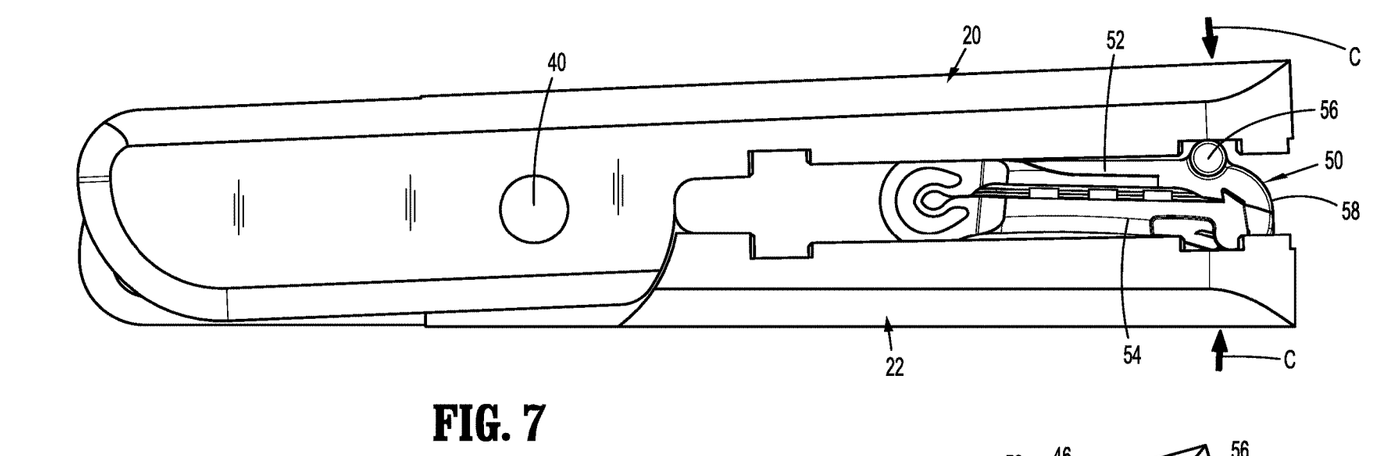
FIG. 7 is a side view of the tool assembly of the ligation clip removal device shown in FIG. 5 with the jaws of the tool assembly in a clamped position and the ligation clip deformed between the jaws to release a latch of the ligation clip.

The elongate body 14 includes a distal portion defining a clevis 18 having spaced arms 18a, 18b. The tool assembly 12 is supported on the clevis 18 and includes a first jaw 20 and a second jaw 22. The first jaw 20 includes a proximal portion defining a cam slot 24 (FIG. 2), a central portion defining a bore 26, and a distal portion defining a clip engagement surface 28. Similarly, the second jaw 22 includes a proximal portion defining a cam slot 32 (FIG. 2), a central portion defining a bore 34 (FIG. 2), and a distal portion defining a clip engagement surface 36. Each of the spaced arms 18a, 18b of the clevis 18 (FIG. 2) defines a bore 38 that receives a pivot member 40. The pivot member 40 extends through the bores 38 in the arms 18a, 18b of the clevis 18 and the bores 26 and 34 of the first and second jaws 20 and 22, respectively, to pivotably secure the first and second jaws 20, 22 of the tool assembly 12 to the distal portion of the elongate body 14 and to pivotably secure the first jaw 20 in relation to the second jaw 22 between an open position (FIG. 3) and clamped position (FIG. 7).

Each of the clip engagement surfaces 28, 36 of the first and second jaws 20, 22, respectively, includes a recess 42 having a longitudinal portion 44 that extends along a longitudinal axis of the first and second jaws 20, 22 and a first transverse portion 46 positioned on a distal portion of the engagement surface 28, 36 of the first and second jaws 20, 22. Each of the longitudinal portions 44 has a first floor and each of the transverse portions 46 defines a second floor that is coplanar with a respective first floor. In some embodiments, the recess 42 defined in each of the clip engagement surfaces 28, 36 of the first and second jaws 20, 22 includes a second transverse portion 48 positioned on a proximal portion of the clip engagement surfaces 28, 36 of the first and second jaws 20, 22, respectively. Although the recess 42 is illustrated to be defined in each of the first and second jaws 20, 22, it is envisioned that the recess 42 can be formed in only one of the first and second jaws 20, 22.

In embodiments, the longitudinal portion 44 of the recesses 42 of the first and the second jaws 20, 22 is dimensioned to receive a ligation clip 50, e.g., a polymeric ligation clip, when the ligation clip 50 is in a latched state. As is known in the art, polymeric ligation clips 50 typically include a first leg 52 and a second leg 54 that is pivotably coupled to the first leg 52. In embodiments, one of the first or second legs 52, 54 of the ligation clip 50 includes a transverse boss 56 and distal ends of the first and second legs 52, 54 define a latch 58. The latch 58 retains the ligation clip 50 in a latched state about tissue (not shown). The longitudinal portion 44 of the recesses 42 are dimensioned to receive the width and length of the first and second legs 52, 54 of the ligation clip 50 and the first transverse portion 46 of the recess 42 is dimensioned to receive the boss 56 of the ligation clip 50 to stabilize the ligation clip 50 within the first and second jaws 20, 22 of the tool assembly 12 to facilitate unlatching of the ligation clip 50 as described in detail below. As used herein, "stabilizing" means prevent twisting and/or substantial lateral movement of the ligation clip within the jaws 20, 22 of the tool assembly 12.

Referring to FIG. 2, the drive member 16 includes a shaft 60 and a cam member 62. The shaft 60 is connected to an actuation device (not shown), e.g., a handle assembly or robotic device, that is operable to cause longitudinal translation of the shaft 60 within the elongate body 14 of the ligation clip removal device 10. When the shaft 60 is moved longitudinally in the directions indicated by arrows AB in FIG. 2, the cam member 62 is moved in relation to the tool assembly 12 within the cam slots 24, 32 of the first and second jaws 20, 22, respectively, to move the first and second jaws 20, 22 between the open and clamped positions.

In embodiments, the actuation device may be supported within a handle assembly (not shown) or a robotic device (not shown).

Figure 3:
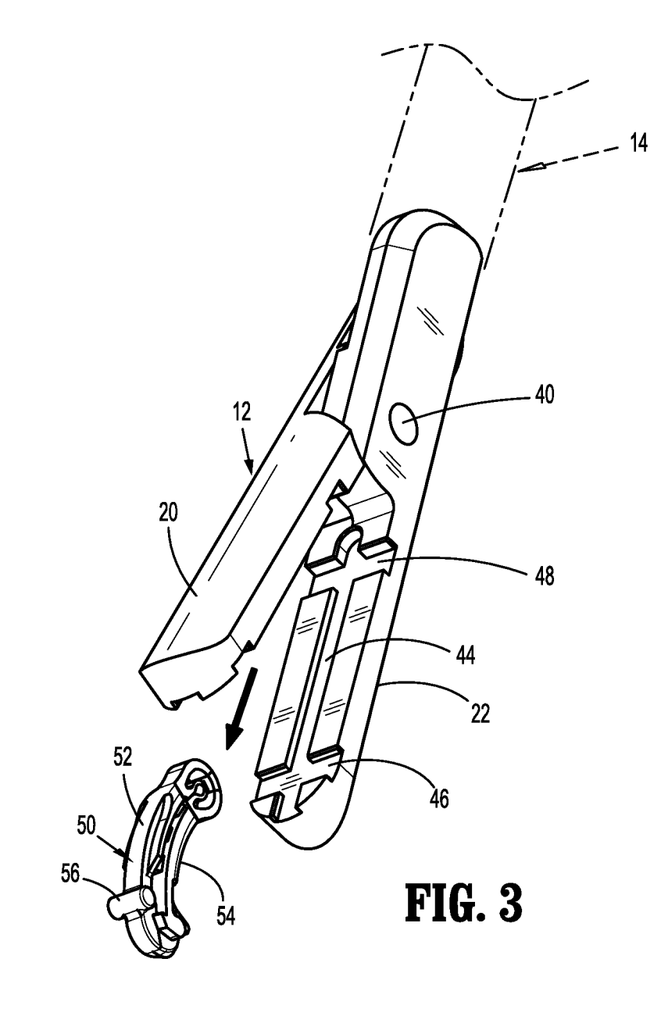
FIG. 3 is a side perspective view of the distal portion of the ligation clip removal device shown in FIG. 2 with the jaws of the tool assembly in an open position and a ligation clip spaced from the jaws in the latched state.
Figure 4:
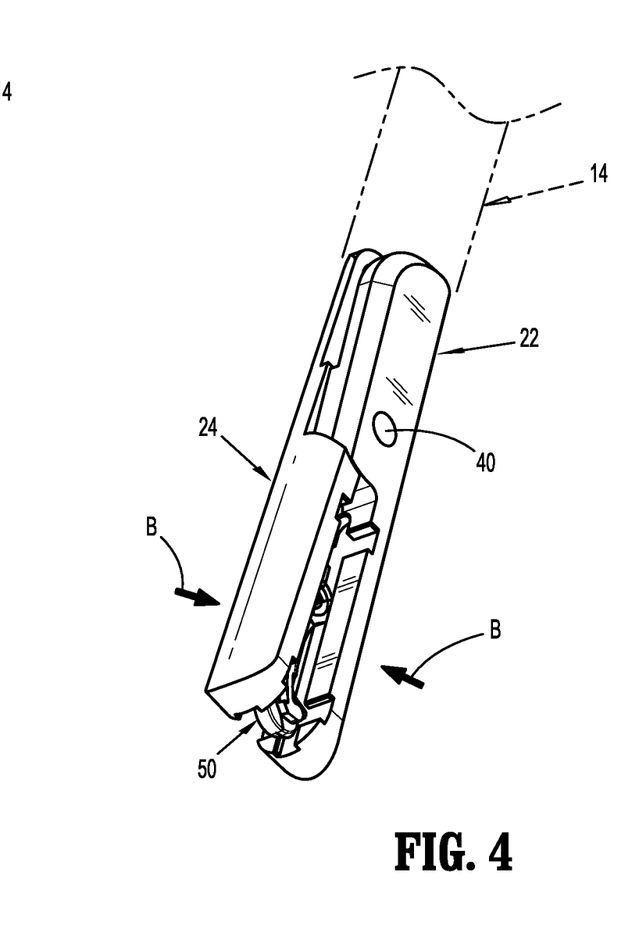
FIG. 4 is a side perspective view of the distal portion of the ligation clip removal device shown in FIG. 3 with the jaws of the tool assembly in the intermediate position and the ligation clip positioned between the jaws in the latched state.
Figures 5, 6:
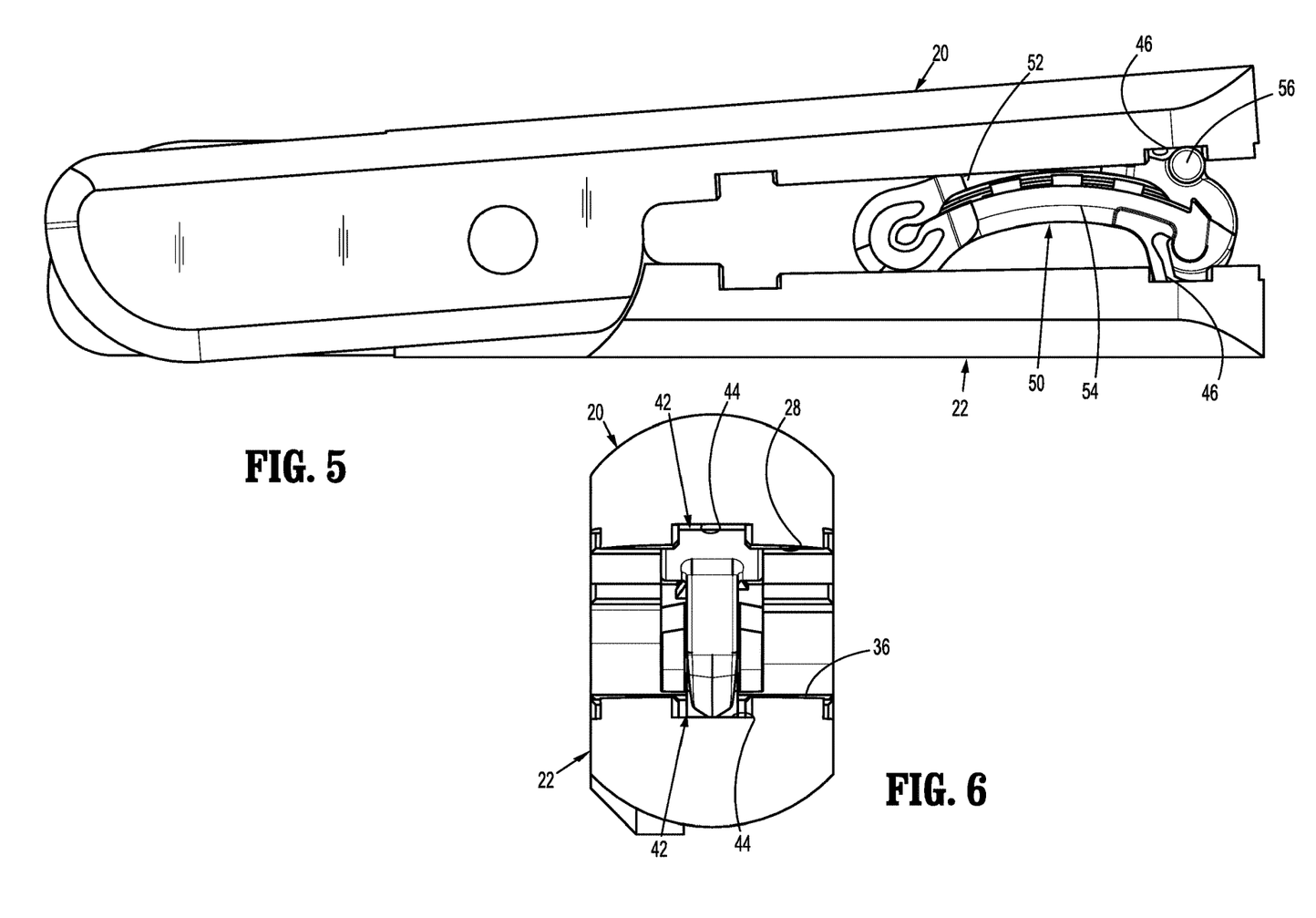
FIG. 5 is a side view of the tool assembly of the ligation clip removal device shown in FIG. 4 with the jaws of the tool assembly in the intermediate position and a ligation clip positioned between the jaws in a latched state.
FIG. 6 is a front end view of the tool assembly the ligation clip removal device shown in FIG. 5 in the intermediate position with the ligation clip positioned between the jaws in the latched state.

Referring to FIGS. 3-6, when a clinician wants to remove a ligation clip 50 from a clamped position about tissue (not shown), the clinician actuates the drive member 16 (FIG. 2) to move the first and second jaws 20, 22 of the tool assembly 12 to an open position (FIG. 3). When the tool assembly 12 is moved to the open position, the tool assembly 12 can be placed about the ligation clip 50 (FIG. 3). When the ligation clip 50 is properly positioned between the jaws 20, 22 of the tool assembly 12, the drive member 16 can be actuated to move the jaws 20, 22 of the tool assembly 12 in the direction indicated by arrows "B" in FIG. 4 from the open position (FIG. 3) to an intermediate position (FIG. 5) to secure the ligation clip 50 between the jaws 20, 22 of the tool assembly 12. In the intermediate position of the first and second jaws 20, 22, the legs 52, 54 of the ligation clip 50 are positioned within the longitudinal portions 44 of the recesses 42 (FIG. 6), the boss 56 of the ligation clip 50 is positioned in the transverse portion 46 of the jaw 20 of the tool assembly, and the ligation clip 50 is frictionally engaged by the jaws 20, 22 to retain the ligation clip in a substantially fixed position between the jaws 20, 22. Sidewalls defining the recesses 42 of the first and the second jaws 20, 22 of the tool assembly 12 prevent and/or minimize twisting and lateral movement of the ligation clip 50 within the tool assembly 12. As shown in FIG. 5, in the intermediate position of the jaws 20, 22 of the tool assembly 12, the ligation clip 50 is not substantially deformed, if deformed at all, and retains its curvature.

Figure 8:
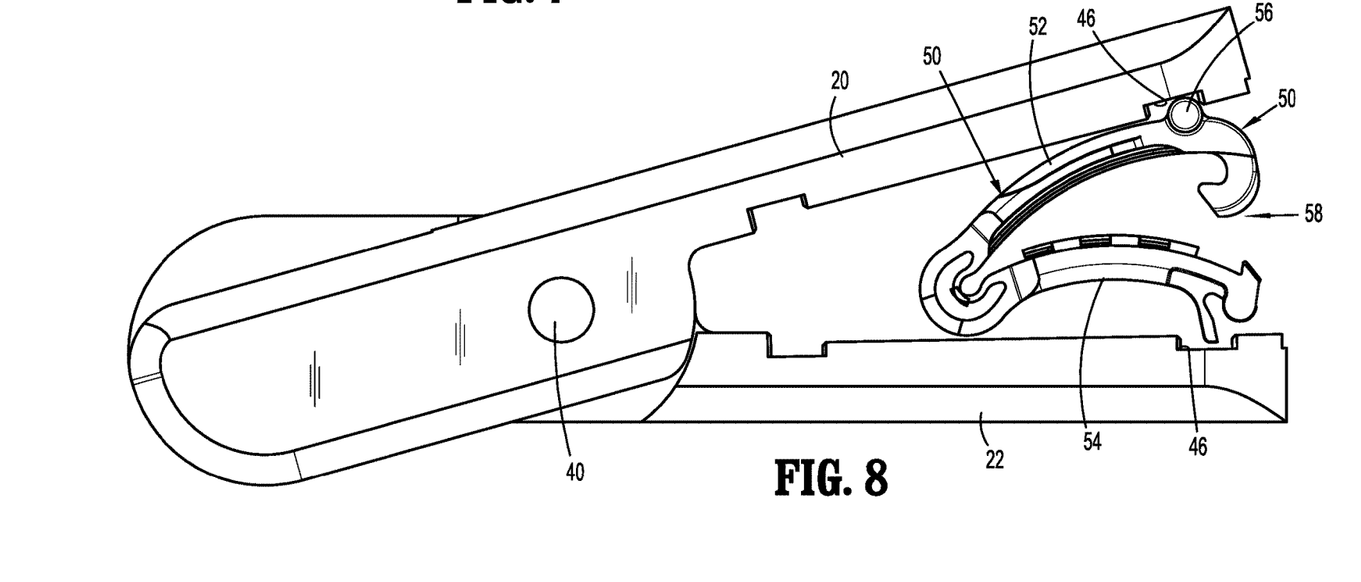
FIG. 8 is a side view of the tool assembly of the ligation clip removal device shown in FIG. 7 with the jaws of the tool assembly in the open position and the ligation clip positioned between the jaws in an unlatched state.

Referring to FIG. 7, when the first and second jaws 20, 22 of the tool assembly 12 are moved to the closed position in the direction indicated by arrows "C", the ligation clip 50 is deformed such that the curvature in the legs 50, 52 is straightened. When this occurs, the latch 58 at the distal ends of the legs 52, 54 disengage from each other to allow the ligation clip to flex to an open position shown in FIG. 8. At this point the ligation clip 50 can be disengaged from the body tissue (not shown) and subsequently removed from the tool assembly 12.

The recesses 42 in the first and the second jaws 20, 22 of the tool assembly 12 maintain alignment of the ligation clip 50 within the jaws 20, 22 of the tool assembly 12 to allow the jaws 20, 22 to straighten the legs 52, 54 of the ligation clip 50 when the tool assembly 12 is moved to the clamped position. This allows the legs 52, 54 of the ligation clip 50 to unlatch from each other so that the ligation clip 50 will open. The ligation clip removal device 10 allows a clinician to quickly and easily remove ligation clips 50 from body tissue.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A ligation clip removal device comprising:
an elongate body defining a longitudinal bore and having a proximal portion and a distal portion, the distal portion of the elongate body including a clevis;
a tool assembly supported on the distal portion of the elongate body, the tool assembly including a first jaw and a second jaw pivotably supported in relation to the first jaw between an open position and a clamped position, each of the first and second jaws pivotably supported on the clevis and including a clip engagement surface, the clip engagement surface of at least one of the first or second jaws defining a recess having a longitudinal portion and a first transverse portion that intersects the longitudinal portion, the longitudinal portion of the recess being configured to receive a leg of a ligation clip and the first transverse portion of the recess being configured to receive a portion of a boss of the ligation clip, wherein the longitudinal portion of the recess has a first floor and the first transverse portion of the recess has a second floor, the first and second floors positioned along a common plane; and
a drive member movable within the longitudinal bore of the elongate body and engaged with the tool assembly, the drive member being movable in relation to the tool assembly to move the first and second jaws between the open and clamped positions;
each of the first and second jaws defining a cam slot and the drive member including a cam member, the cam member being positioned within the cam slots of the first and second jaws such that movement of the drive member in relation to the tool assembly moves the first and second jaws between the open and clamped positions;
wherein each of the first and second jaws defines the recess.

2. The ligation clip removal device of claim 1, wherein the recess includes a second transverse portion that is spaced from the first transverse portion and intersects the longitudinal portion.

3. The ligation clip removal device of claim 2, wherein the first transverse portion of the recess is perpendicular to the longitudinal portion.

4. A tool assembly comprising:
a first jaw and a second jaw pivotably supported in relation to the first jaw between an open position and a clamped position, each of the first and second jaws including a clip engagement surface, the clip engagement surface of at least one of the first or second jaws defining a recess having a longitudinal portion and a first transverse portion that intersects the longitudinal portion, the longitudinal portion of the recess being positioned and configured to receive a leg of a ligation clip and the first transverse portion of the recess being positioned and configured to receive a portion of a boss of the ligation clip, wherein the longitudinal portion of the recess has a first floor and the first transverse portion of the recess has a second floor, the first and second floors positioned along a common plane;
each of the first and second jaws defining a cam slot that is configured to receive a cam member, wherein movement of the cam member in relation to the first and second jaws causes the first and second jaws to move between the open position and the clamped position;
wherein each of the first and second jaws defines the recess.

5. The tool assembly of claim 4, wherein the recess includes a second transverse portion that is spaced from the first transverse portion and intersects the longitudinal portion.

6. The tool assembly of claim 4, wherein the first transverse portion of the recess is perpendicular to the longitudinal portion of the recess.

7. A ligation clip removal device comprising:
an elongate body having a proximal portion and a distal portion;
a tool assembly supported on the distal portion of the elongate body, the tool assembly including a first jaw and a second jaw pivotably supported in relation to the first jaw between an open position and a clamped position, each of the first and second jaws including a clip engagement surface, the clip engagement surface of each of the first and second jaws defining a recess having a longitudinal portion and a first transverse portion that intersects the longitudinal portion, the longitudinal portions of the recesses being configured to receive a leg of a ligation clip and the first transverse portions of the recesses being configured to receive a portion of a boss of the ligation clip, wherein the longitudinal portion of the recess of the first jaw has a first floor and the first transverse portion of the recess of the first jaw has a second floor, the first and second floors positioned along a common plane; and
a drive member engaged with the tool assembly, the drive member being movable in relation to the tool assembly to move the first and second jaws between the open and clamped positions.

8. The ligation clip removal device of claim 7, wherein the distal portion of the elongate body includes a clevis, each of the first and second jaws being pivotably supported on the clevis.

9. The ligation clip removal device of claim 8, wherein each of the first and second jaws defines a cam slot and the drive member includes a cam member, the cam member being positioned within the cam slots of the first and second jaws such that movement of the drive member in relation to the tool assembly moves the first and second jaws between the open and clamped positions.

10. The ligation clip removal device of claim 7, wherein the first transverse portion of the recess of the first jaw is perpendicular to the longitudinal portion of the recess of the first jaw.

* * * * *